(12) United States Patent
Müller et al.

(10) Patent No.: US 9,651,501 B2
(45) Date of Patent: May 16, 2017

(54) DEVICE AND METHOD FOR RECORDING CONTAMINATIONS IN A HYDRAULIC SYSTEM

(71) Applicant: Airbus Operations GmbH, Hamburg (DE)

(72) Inventors: Gerhard Müller, Grafing (DE); Sumit Paul, München (DE); Andreas Helwig, München (DE); Volker Baumbach, Ritterhude (DE)

(73) Assignee: Airbus Operations GmbH, Hamburg (DE)

( * ) Notice: Subject to any disclaimer, the term of this patent is extended or adjusted under 35 U.S.C. 154(b) by 0 days.

(21) Appl. No.: 14/448,724

(22) Filed: Jul. 31, 2014

(65) Prior Publication Data

US 2015/0021482 A1   Jan. 22, 2015

Related U.S. Application Data

(63) Continuation of application No. PCT/EP2013/051609, filed on Jan. 29, 2013.

(30) Foreign Application Priority Data

Jan. 31, 2012   (DE) .................. 10 2012 100 794

(51) Int. Cl.
*G01N 21/89* (2006.01)
*G01N 15/02* (2006.01)
(Continued)

(52) U.S. Cl.
CPC ..... *G01N 21/8914* (2013.01); *G01N 15/0205* (2013.01); *G01N 21/314* (2013.01);
(Continued)

(58) Field of Classification Search
CPC ............. G01N 21/3577; G01N 21/359; G01N 21/8507; G01N 21/31; G01N 21/33;
(Continued)

(56) References Cited

U.S. PATENT DOCUMENTS 3,539,804 A   11/1970   Billetdeaux et al.
4,013,953 A *   3/1977   Skala .......................... 324/130
(Continued)

FOREIGN PATENT DOCUMENTS

DE   10 2006 060 138 A1   6/2008
DE   10 2006 060 138 B4   1/2009
(Continued)

OTHER PUBLICATIONS

Weyer, L.G. and Lo, S.-C., "Spectra-Structure Correlations in the Near-infrared", 2006, Handbook of Vibrational Spectroscopy, pp. 1817-1837.*

(Continued)

*Primary Examiner* — David Porta
*Assistant Examiner* — Blake Riddick
(74) *Attorney, Agent, or Firm* — Jenkins, Wilson, Taylor & Hunt, P.A.

(57) ABSTRACT

The invention relates to a contamination recording apparatus (12) for recording contaminations in a flowing hydraulic fluid (10) to be examined in aircraft (11*a*), which comprises a conveying device (14) for conveying the flowing hydraulic fluid (10), a light source (34) for exposing the hydraulic fluid (10) flowing in the conveying device (14) to light (46), and a detection device (36) for recording a fraction of the light (46) absorbed by the exposed hydraulic fluid (10), the light source (34) being formed in order to emit light (46) having a wavelength in the near-infrared range. The invention furthermore relates to a hydraulic system (11) equipped with such a contamination recording apparatus (12) and to an (Continued)

aircraft (11a), and also to a method for recording contaminations in a hydraulic fluid (10) flowing in a hydraulic system (11) of an aircraft (11a).

11 Claims, 9 Drawing Sheets

(51) Int. Cl.
   *G01N 33/28* (2006.01)
   *G01N 21/31* (2006.01)
   *G01N 21/35* (2014.01)
   *G01N 21/85* (2006.01)
   *G01N 21/3577* (2014.01)
   *G01N 21/359* (2014.01)
   G01N 21/03 (2006.01)
   G01N 21/09 (2006.01)
   G01N 21/53 (2006.01)
   G01N 21/64 (2006.01)
   G01N 21/94 (2006.01)

(52) U.S. Cl.
   CPC ....... *G01N 21/359* (2013.01); *G01N 21/3577* (2013.01); *G01N 21/85* (2013.01); *G01N 33/2847* (2013.01); *G01N 33/2852* (2013.01); *G01N 33/2876* (2013.01); G01N 21/0317 (2013.01); G01N 21/09 (2013.01); G01N 21/53 (2013.01); G01N 21/643 (2013.01); G01N 21/94 (2013.01); G01N 2021/3148 (2013.01); G01N 2201/0214 (2013.01); G01N 2201/062 (2013.01); G01N 2201/0621 (2013.01); G01N 2201/0627 (2013.01); G01N 2201/0697 (2013.01); G01N 2201/06113 (2013.01)

(58) Field of Classification Search
   CPC ...... G01N 21/35; G01N 21/53; G01N 21/534; G01N 33/2876; G01N 33/2835
   USPC ........ 250/341.1, 269.1, 343, 339.11, 339.12, 250/573, 239, 341.5, 340; 356/51, 337, 356/442, 70
   See application file for complete search history.

(56) References Cited

U.S. PATENT DOCUMENTS

| | | | | |
|---|---|---|---|---|
| 4,499,376 A * | 2/1985 | Frost et al. | ................. | 250/341.5 |
| 5,239,860 A * | 8/1993 | Harris | ................. | G01N 21/3577 123/1 A |
| 5,438,420 A * | 8/1995 | Harwick et al. | ............. | 356/440 |
| 5,936,715 A * | 8/1999 | Shapanus et al. | ............. | 356/70 |
| 6,151,108 A * | 11/2000 | Kwon et al. | .................... | 356/70 |
| 6,331,704 B1 * | 12/2001 | Owen | ..................... | 250/339.11 |
| 6,452,179 B1 * | 9/2002 | Coates et al. | ............ | 250/339.09 |
| 7,049,831 B2 * | 5/2006 | Wooton et al. | ............... | 324/698 |
| 7,078,910 B2 * | 7/2006 | Hirthe et al. | ................. | 324/446 |
| 7,593,101 B2 * | 9/2009 | Yakimoski et al. | .......... | 356/246 |
| 7,840,360 B1 * | 11/2010 | Micheels et al. | ............... | 702/25 |
| 2002/0180972 A1 * | 12/2002 | Ansari et al. | ................. | 356/336 |
| 2003/0047135 A1 * | 3/2003 | Kansakoski | ....... | G01N 21/3563 118/665 |
| 2003/0141459 A1 * | 7/2003 | Hegazi et al. | ............. | 250/461.1 |
| 2003/0180958 A1 * | 9/2003 | Schilowitz et al. | ............ | 436/60 |
| 2003/0189711 A1 * | 10/2003 | Orr | .......................... | G01J 3/42 356/484 |
| 2003/0222656 A1 * | 12/2003 | Phillips et al. | ............... | 324/605 |
| 2004/0084623 A1 * | 5/2004 | Long et al. | .............. | 250/339.12 |
| 2004/0106204 A1 * | 6/2004 | Chimenti et al. | ............ | 436/55 |
| 2004/0218176 A1 * | 11/2004 | Shammal et al. | ............ | 356/326 |
| 2005/0159656 A1 * | 7/2005 | Hockersmith | ..... | A61B 5/14532 600/315 |
| 2005/0240107 A1 * | 10/2005 | Alfano | ................. | A61B 5/0059 600/476 |
| 2006/0124552 A1 * | 6/2006 | Nagai et al. | .................. | 210/689 |
| 2007/0120281 A1 * | 5/2007 | Khusid et al. | ................. | 264/11 |
| 2008/0156088 A1 * | 7/2008 | Hsu | ....................... | E21B 49/10 73/152.23 |
| 2008/0218733 A1 * | 9/2008 | Benes | ...................... | G01J 3/02 356/51 |
| 2010/0026988 A1 * | 2/2010 | Cros et al. | ..................... | 356/51 |
| 2010/0160750 A1 * | 6/2010 | White | ................. | A61B 5/0075 600/322 |
| 2012/0170025 A1 | 7/2012 | Cros et al. | | |

FOREIGN PATENT DOCUMENTS

| | | |
|---|---|---|
| EP | 2 378 277 | 10/2011 |
| WO | WO 2009/080049 | 7/2009 |
| WO | WO 2010/139965 | * 12/2010 |
| WO | WO 2013/113666 | 8/2013 |

OTHER PUBLICATIONS

Paul, S. et al: Chemical Contamination Sensor for Phosphate Ester Hydraulic Fluids; International Journal of Aerospace Engineering vol. 2010 (2010), Article ID 156281.

Paul, S. et al: Multi-Parameter Monitoring System for Hydraulic Fluids; Technisches Messen 78 (2011) 5 / DOI 10.1524/teme.2011.0117, Oldenbourg Wissenschaftsverlag.

International Search Report for Application No. PCT/EP 2013/051609 dated Mar. 22, 2013.

German Office Action for Application No. 10 2012 100 794.2 dated Oct. 2, 2012.

Written Opinion for Application No. PCT/EP2013/051609 dated Mar. 22, 2013.

* cited by examiner

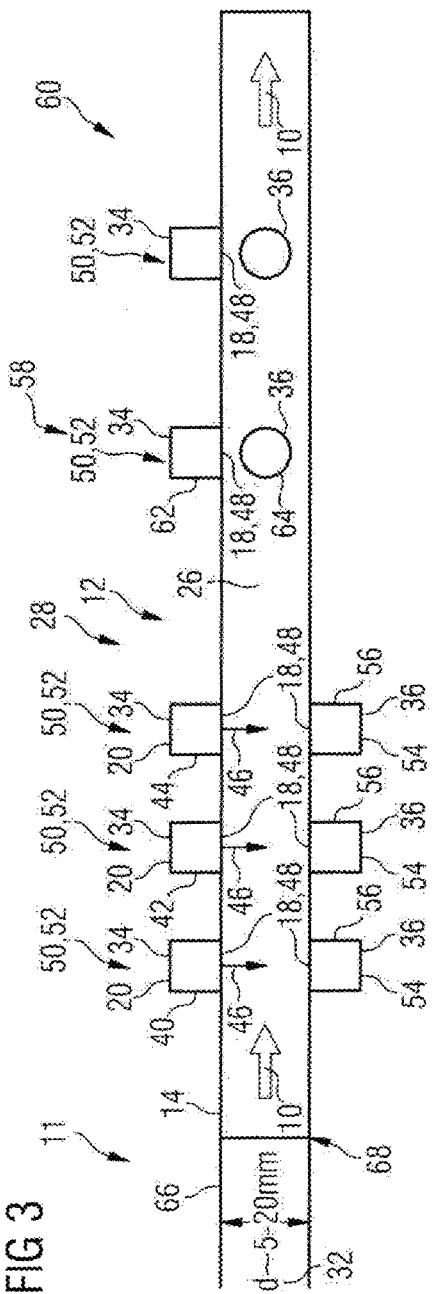

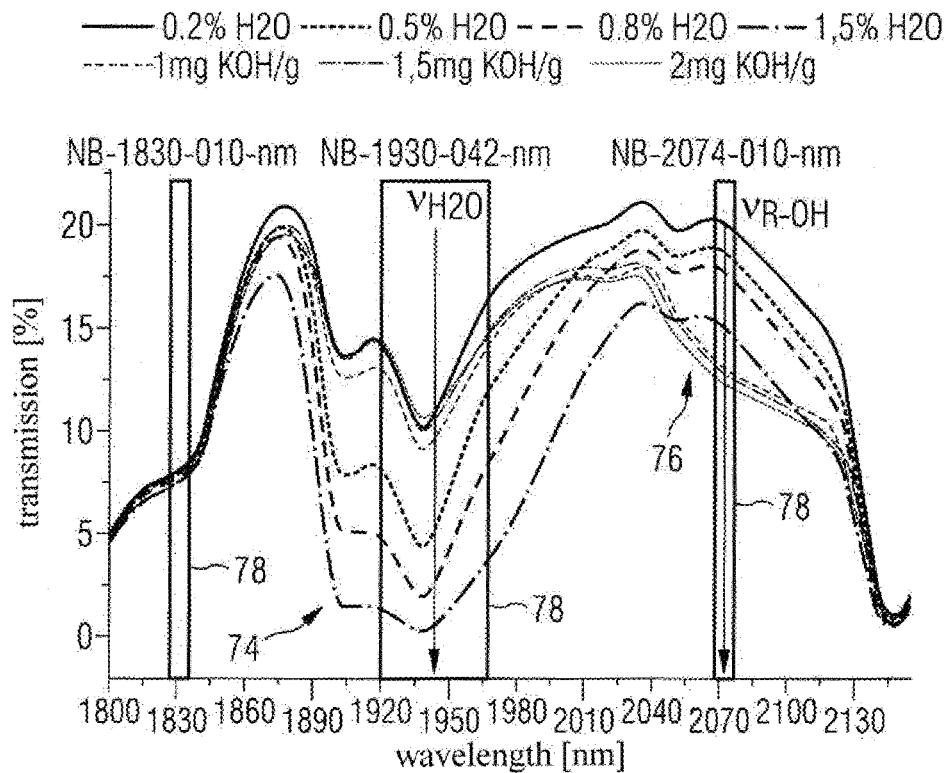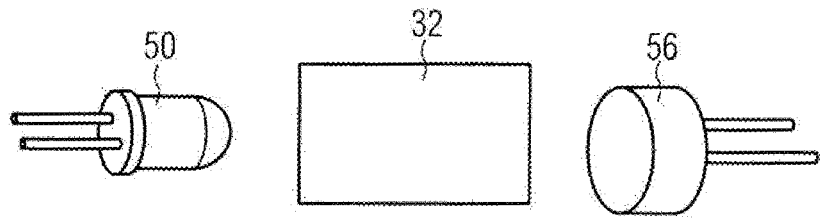

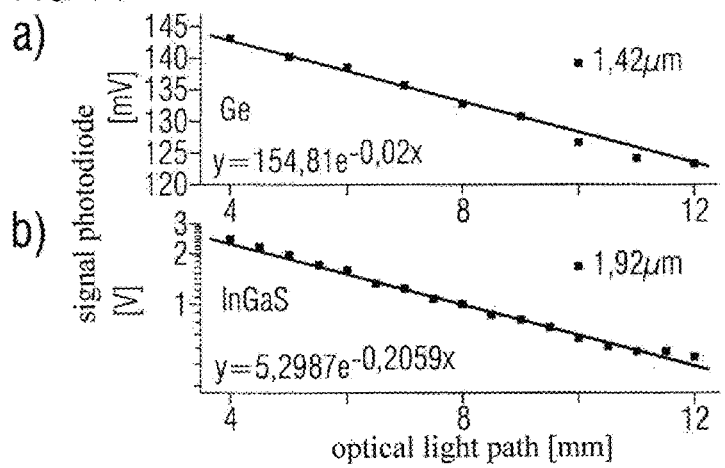
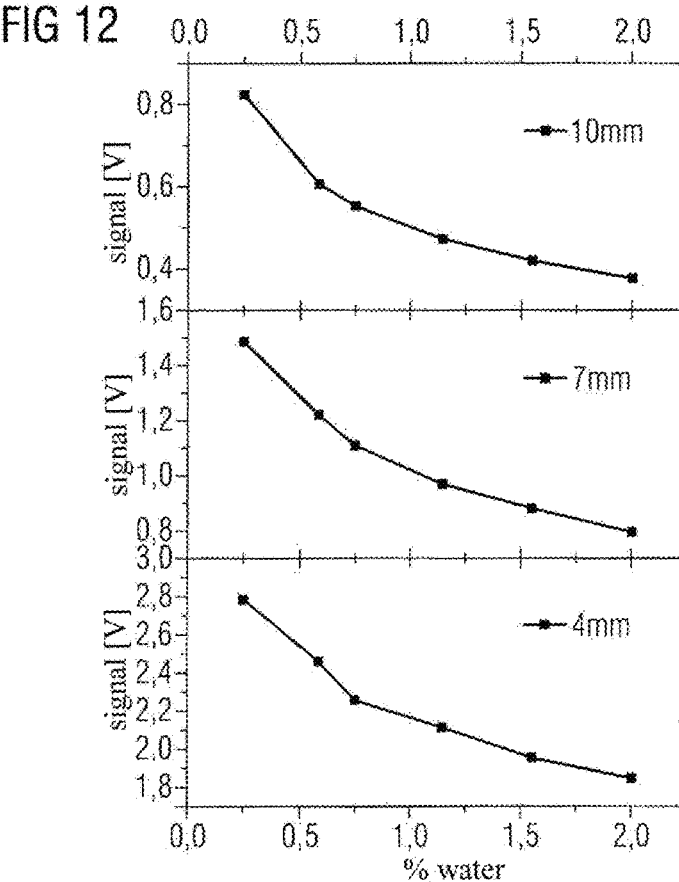

DEVICE AND METHOD FOR RECORDING CONTAMINATIONS IN A HYDRAULIC SYSTEM

TECHNICAL FIELD

The invention relates to a contamination recording apparatus for recording contaminations in a flowing hydraulic fluid, particularly in vehicles, more particularly in aircraft, to a hydraulic system equipped with such a contamination recording apparatus, and to an aircraft which comprises the hydraulic system. The invention furthermore relates to a method for recording contaminations in a hydraulic fluid flowing in a hydraulic system, in particular of a vehicle or an aircraft.

BACKGROUND

Previously to this end, for example, when the aircraft for checking has been on the ground, samples of the hydraulic fluid have been taken and these samples have been sent to chemical laboratories in order to be able to check the quality of the hydraulic fluid. On the one hand, such analysis takes a long time and can generate high costs. On the other hand, samples of the hydraulic fluid cannot be taken constantly, and therefore continuous monitoring of the hydraulic fluid cannot be ensured by such a method.

It is therefore desirable to use monitoring methods which can monitor the hydraulic fluid continuously in respect of its quality, without the aircraft having to be on the ground.

For example, sensors are used which record the electrical or dielectric properties of the hydraulic fluid. On the other hand, however, optical sensors are preferable since the recorded data correlate directly with the chemical properties such as the water content and the acid number. The Applicant has previously experimented in this field with sensors which expose the hydraulic fluid to light from the mid-infrared range (3000 nm to 5000 nm), so as to acquire the absorption spectra of the exposed hydraulic fluid.

These absorption spectra can be used to determine the chemical composition of the hydraulic fluid.

SUMMARY

It is therefore an object of the invention to provide an apparatus and a method for monitoring the quality of a hydraulic fluid, which can be integrated into a hydraulic system.

This object is achieved by a contamination recording apparatus having the features described herein.

A hydraulic system which comprises this contamination recording apparatus, and an aircraft having the contamination recording apparatus or having the hydraulic system, are the subject-matter of the co-ordinate claims. Furthermore, a method for recording contaminations in a hydraulic system is the subject-matter of the co-ordinate claim.

Advantageous configurations of the invention are the subject-matter of the dependent claims.

A contamination recording apparatus for recording contaminations in a flowing hydraulic fluid to be examined, particularly in vehicles, more particularly in aircraft, comprises at least one conveying device, usable as part of a hydraulic system, for conveying the flowing hydraulic fluid, at least one light source for exposing the hydraulic fluid flowing in the conveying device to light, and at least one detection device for recording a fraction of the light absorbed by the exposed hydraulic fluid, the at least one light source being formed in order to emit light having a wavelength in the near-infrared range.

With this structure, the light source can expose the hydraulic fluid to light while it is flowing in the conveying device, that is to say while the hydraulic fluid is being used. Vibrations of the molecules present in the hydraulic fluid are excited by the exposure to light. Each vibration of a particular molecule is in this case excited by a very particular energy and thereby absorbs a particular intensity fraction of the incident light in a corresponding energy range depending on the concentration. The detection device records how much light has been absorbed in which energy range, i.e. an absorption spectrum, so that the concentration and species of the absorbing molecule parts can be determined.

In this case, however, the light source preferably does not emit mid-infrared light (MIR) as in previous experiments, but instead light in the near-infrared range (NIR), that is to say with a shorter wavelength and therefore a higher energy. NIR light is absorbed less strongly by liquids and therefore has a greater penetration depth than MIR light into a hydraulic fluid to be examined. Although the absorption of the light intensity of NIR light by the molecular vibrations is significantly less than that of MIR light, and therefore also results in absorption spectra having a significantly reduced intensity, the Applicant has nevertheless discovered by experiments that the absorption in particular energy ranges is strong enough to be able to detect a chemical change in the hydraulic fluid.

By the use of NIR light, it is therefore possible to provide a wider light path and integrate the contamination recording apparatus even in an existing hydraulic system, of an aircraft for example, without impeding the flow of the hydraulic fluid.

In a preferred configuration, the conveying device comprises a conveying channel for conveying the hydraulic fluid having an internal diameter of >2 mm, in particular from 2 mm to 25 mm, more particularly from 5 mm to 20 mm.

It is therefore possible to convey the hydraulic fluid through a relatively wide conveying channel without a constriction, and therefore advantageously to avoid a pressure drop of the hydraulic fluid.

Preferably, the conveying device is formed in order to convey the hydraulic fluid under high pressure. This means that the conveying device can also advantageously withstand a high pressure of the hydraulic fluid, without thereby being destroyed. It can therefore advantageously be integrated into a hydraulic system, for example of an aircraft, in which the hydraulic fluid conventionally flows with a high pressure.

Also advantageously, the conveying device is formed in order to convey a hydraulic fluid based on phosphate esters. Phosphate esters have the advantage that they are fire-resistant, for which reason they are suitable in particular for use in aircraft. They are however highly toxic, for which reason the conveying device is advantageously formed in such a way that, for example, escape of the hydraulic fluid which is conveyed under high pressure through the conveying device can substantially be avoided.

Advantageously, the conveying device comprises at least one region which is optically transparent for infrared radiation. The light source can therefore advantageously be arranged outside the conveying device while nevertheless advantageously projecting NIR light into the hydraulic fluid flowing in the conveying device.

Particularly advantageously, the optically transparent region is formed by a high-pressure stable window, so that the optically transparent region can preferably also withstand the high pressure of the hydraulic fluid and damage due to pressure can therefore advantageously be avoided. In a particularly preferred configuration, the optically transparent region is formed by a sapphire window. Sapphire has the advantage that it is advantageously optically transparent in the NIR range and, at the same time, withstands extreme loads.

Preferably, the light source and the detection device are arranged on the optically transparent region in such a way that at least a fraction of the light transmitted through the hydraulic fluid is incident on the detection device. Particularly preferably in this case, the light source and the detection device are arranged on the conveying device, or the optically transparent region.

Preferably, the light source is formed in order to emit light having a wavelength of from 700 nm to 2500 nm, which corresponds to the NIR range.

In a particularly preferred configuration, the light source is in this case formed by an LED and/or a laser. The LED and/or the laser is preferably selected in such a way that the light emitted by it has an emission peak in the wavelength range of from 1350 nm to 1450 nm and/or from 1900 nm to 2000 nm. This is because the prominent vibration absorptions of water are to be found in the range around 1400 nm and around 1940 nm. It is advantageous in particular for the light to be projected into the hydraulic fluid with a high intensity in these ranges.

Preferably, a plurality of light sources are provided for exposing the hydraulic fluid, which project light in different wavelength ranges onto the hydraulic fluid. In this way, special vibration absorptions can advantageously be observed particularly accurately.

For example, a first light source is formed in such a way that it emits light in the wavelength range of alcohol absorptions, that is to say OH absorptions, which preferably lie in the wavelength range of from 2020 nm to 2150 nm.

Furthermore, for example, a second light source is formed in such a way that it emits light in the wavelength range of water absorptions, particularly preferably in the wavelength range of from 1880 nm to 2000 nm.

In an advantageous configuration, a third light source is provided which emits light in a wavelength range in which neither alcohol absorptions nor water absorptions are to be found, preferably in the wavelength range of from 1820 nm to 1840 nm. This third light source may preferably be used as a reference light source, so as to normalize the absorptions in the other ranges advantageously to the light transmissivity of the hydraulic fluid.

Advantageously, a separate detection device is assigned to each light source. In a particularly preferred configuration, the detection devices are formed in such a way that they are optimized for the detection of light in the wavelength range of the light emitted by the respectively assigned light source.

Advantageously, the detection device or each detection device comprises a detector for recording light having a wavelength in the near-infrared range, that is to say particularly in the range of from 700 nm to 2500 nm.

In a preferred configuration, the detector is a photodiode formed of semiconductor material, in particular InGaAs or Ge. Semiconductor materials have the advantage that they preferably offer a high optical power, a long lifetime and low costs. Advantageously, a photodiode consisting of InGaAs is used for recording light in the wavelength region of 1940 nm, while a photodiode consisting of Ge is used for recording light in the wavelength range of 1400 nm.

In a preferred configuration, an acid number monitoring device for monitoring an acid number of the hydraulic fluid is arranged on the conveying device. Hydraulic fluids, in particular phosphate esters, which are used for example as hydraulic fluids in aviation, are very hygroscopic and therefore absorb a relatively large amount of water. Furthermore, these hydraulic fluids are subjected to high temperatures during operation. The combination of the absorbed water with the elevated temperatures results in the phosphate esters cracking and reacting to form acids. Depending on the acid content, it is therefore advantageously possible to determine whether the chemical quality of the hydraulic fluid is still high enough for further use in an aircraft. The acid number (Total Acid Number, TAN) corresponds in this case to the mass of base, for example KOH, which is required in order to neutralize a particular mass of hydraulic fluid.

In order to monitor the acid number of the hydraulic fluid, a UV light source which is formed in order to expose the hydraulic fluid to ultraviolet light, and is formed in particular by an LED and/or a laser, is advantageously arranged on the conveying device. Furthermore, a UV detection device is advantageously arranged on the conveying device. If UV light is projected into the hydraulic fluid, electrons in the acid molecules of the hydraulic fluid are advantageously energetically excited, and during decay fluorescent light is emitted which can preferably be recorded by the UV detection device. Particularly preferably, the UV detection device is formed by a silicon photodiode or comprises a silicon photomultiplier having a bandpass filter, which preferably transmits the fluorescent light only in the expected energy range.

Furthermore, a particle recording device for recording particles contained in the hydraulic fluid is preferably provided. This particle recording device preferably comprises a light source for exposing the hydraulic fluid to ultraviolet, visible or NIR light, for example, and is formed in particular from a laser and/or an LED. Furthermore, the particle recording device advantageously comprises a detection device, in particular a photodiode, which can record light that is scattered by the particles contained in the hydraulic fluid. In this case, the detection device is advantageously arranged at an angle of from 40° to 140° with respect to the radiation direction of the light, so as preferably to detect preferably only scattered light, but not light transmitted rectilinearly through the hydraulic fluid.

A hydraulic system for conveying a hydraulic fluid from a fluid source to a fluid sink, or vice versa, comprises at least one hydraulic fluid line and at least one contamination recording apparatus as described above. The hydraulic fluid conveyed in the hydraulic system can therefore be monitored continuously for contaminations and chemical quality during operation.

Preferably, the internal diameters of the at least one hydraulic fluid line and of a conveying channel of the contamination recording apparatus are substantially equal. The internal diameter of a conveying region for the hydraulic fluid therefore preferably does not vary, and advantageously no pressure drop takes place at a constriction.

Furthermore, a coupling device is advantageously provided for coupling and/or uncoupling the contamination recording apparatus. For example, such a coupling device may be formed by valves, so that a piece of the hydraulic fluid line can be removed simply and advantageously replaced by the conveying device of the contamination recording apparatus. The contamination recording apparatus can thereby advantageously be integrated particularly simply into an already existing hydraulic system, for example in an aircraft.

A particularly preferred configuration of an aircraft comprises the contamination recording apparatus as described above, or the hydraulic system described above.

In a method for recording contaminations in a hydraulic fluid flowing in a hydraulic system, in particular of a vehicle, more particularly of an aircraft, a hydraulic fluid line for conveying the hydraulic fluid in the hydraulic system is first provided, then a contamination recording apparatus which comprises a conveying device for conveying the hydraulic fluid flowing in the hydraulic system, a light source for exposing the hydraulic fluid flowing in the conveying device to light, and a detection device, which is formed in order to record a light intensity fraction absorbed by the exposed hydraulic fluid, is coupled. The flowing hydraulic fluid is then exposed to light having a wavelength in the NIR range and the fraction of the light which is absorbed by the exposed hydraulic fluid is recorded. The steps are repeated and the results are compared, so as to be able to record changes in the hydraulic fluid continuously.

Advantageously, the contamination recording apparatus is coupled to the hydraulic system in such a way that at least one hydraulic fluid line of the hydraulic system is replaced by the conveying device of the contamination recording apparatus. In this case, it is advantageous to provide a contamination recording apparatus which has a conveying channel whose internal diameter is substantially equal to the internal diameter of the hydraulic fluid line. In particular, a conveying channel is used which has an internal diameter >2 mm, more particularly from 2 mm to 25 mm, more particularly from 5 mm to 25 mm. Thus, stagnation of the hydraulic fluid can preferably be avoided in the region of the hydraulic system in which the hydraulic fluid line has been replaced by the contamination recording apparatus.

Preferably, the flowing hydraulic fluid is exposed to light having a wavelength in the range of from 700 nm to 2500 nm, in particular to light in the range of alcohol absorptions, for example in the wavelength range of from 2020 nm to 2150 nm, and/or in the range of water absorptions, for example in the wavelength range of from 1880 nm to 2000 nm, and/or in a reference range, for example in a wavelength range of from 1820 nm to 1840 nm.

The reference range is advantageously selected in such a way that there are no absorptions therein by the contaminations to be recorded, and therefore the total light transmissivity of the hydraulic fluid for the incident light can preferably be determined in this reference range and the recorded absorptions can advantageously be normalized accordingly.

Preferably, the acid number of the hydraulic fluid and/or the particle count of particles flowing in the hydraulic fluid is recorded.

BRIEF DESCRIPTION OF THE DRAWINGS

A preferred configuration of the invention will be explained in more detail below with the aid of the appended drawings, in which:

FIG. 3 shows the structure of the contamination recording apparatus of FIG. 1;

FIG. 4 shows a sensor system having variable optical path lengths;

FIG. 9 shows absorption spectra of the hydraulic fluid for contamination with water or acid and a selection of suitable wavelength ranges for monitoring the contaminations;

FIG. 10 shows the relative arrangement of a light source, a conveying device for conveying the hydraulic fluid and a photodiode;

FIG. 11 shows the dependency of the signal intensity at a photodiode on the length of the optical path;

FIG. 12 shows the dependency of the signal intensity on the contamination with water, as a function of the respective length of the optical path;

DETAILED DESCRIPTION

Figure 1:
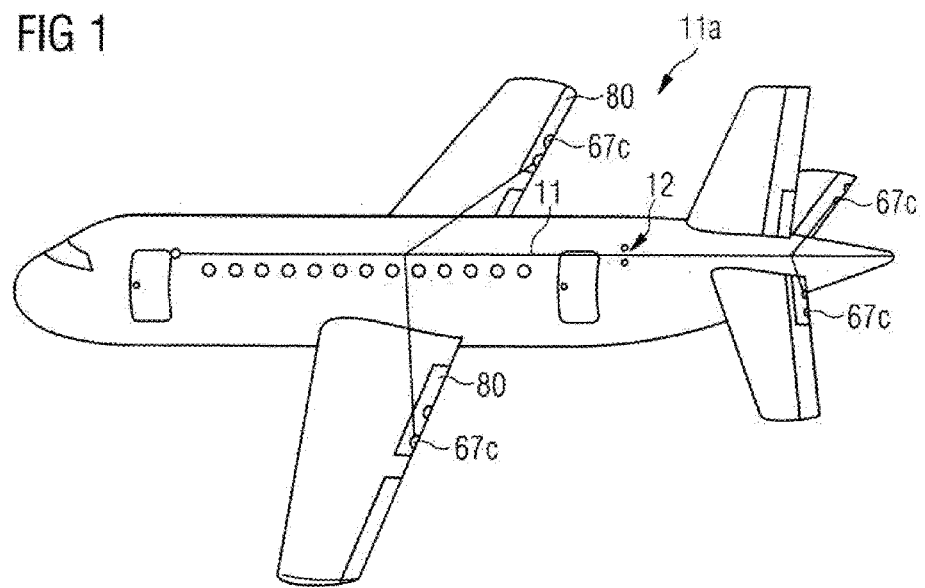
FIG. 1 shows an aircraft having a hydraulic system and a contamination recording apparatus.
Figure 2:
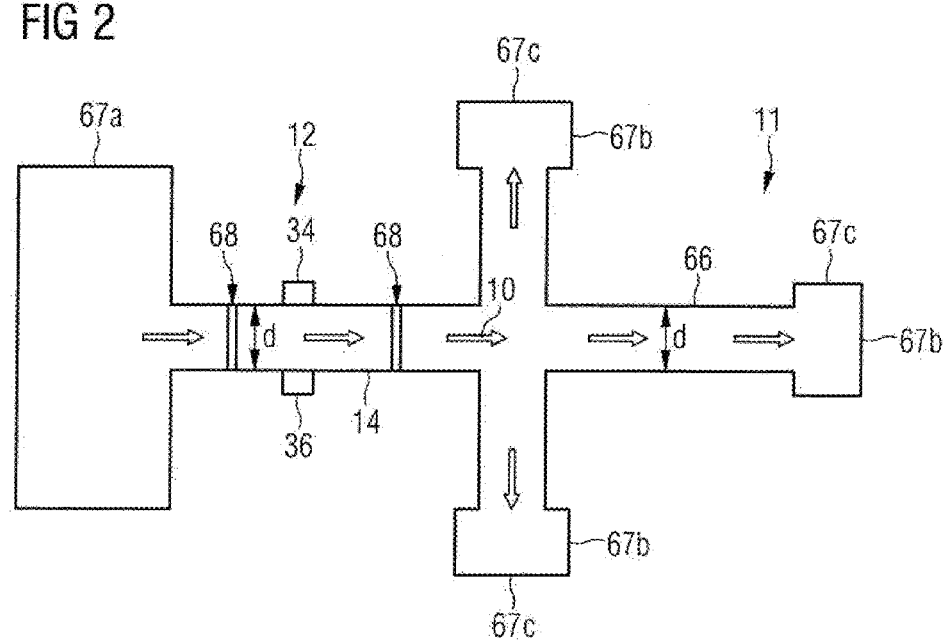
FIG. 2 shows the hydraulic system of FIG. 1 in greater detail.

In order to record contaminations in hydraulic fluids 10, which in particular, as shown in FIG. 1 and FIG. 2, are intended to be used in hydraulic systems 11 in aircraft 11a, the Applicant developed an earlier contamination recording apparatus 12 which theoretically can record contaminations in the hydraulic fluid 10 while the hydraulic fluid 10 is flowing through a conveying device 14, for example a conveying tube. This contamination recording apparatus 12 operates with light in the mid-infrared range (MIR light) 16 and is explained in more detail in FIGS. 13 to 19 for explanatory purposes.

The central concept of the earlier contamination recording apparatus 12 is that O—H absorptions in infrared spectra in the range of 3500 cm$^{-1}$ (about 2850 nm) are recorded, and contamination of the hydraulic fluid with water and/or with acid groups can be deduced with the aid of the change of the absorption in this range.

Figure 13:
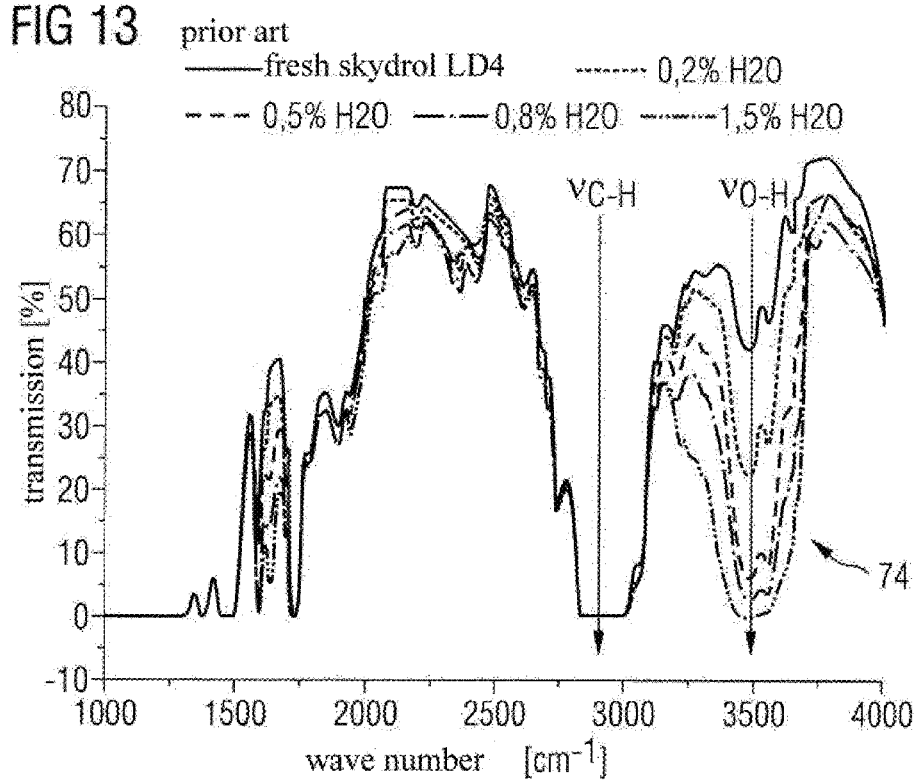
FIG. 13 shows overview spectra in the MIR range of hydraulic fluid contaminated with water.

FIG. 13 in this case shows absorption spectra of a hydraulic fluid 10, namely Skydrol, in the range of from 1000 cm$^{-1}$ to 4000 cm$^{-1}$, the intensity of the transmitted light being plotted on the y axis. In the range around 2800 cm$^{-1}$, a prominent vibration absorption by C—H constituents can be seen, while a prominent vibration absorption by O—H constituents occurs in the range around 3500 cm$^{-1}$. The absorption in the range around 3500 cm$^{-1}$, i.e. of the O—H bands, becomes stronger when more water is added to Skydrol.

Figure 14:
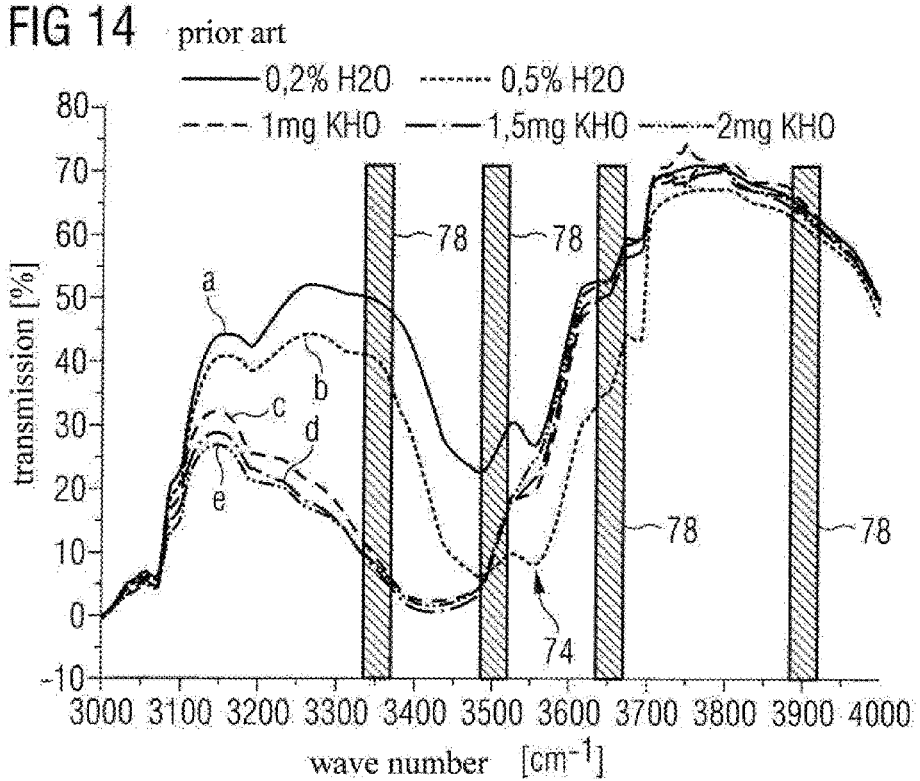
FIG. 14 shows detail spectra of the hydraulic fluid, contaminated with acid, and a selection of suitable monitoring ranges.

FIG. 14 shows a detail range between 3000 cm$^{-1}$ and 4000 cm$^{-1}$ of the spectrum of FIG. 13 to which a water concentration of 0.2% is to be assigned, and further absorption spectra of compositions of Skydrol contaminated with 0.2% water, with additional acid contaminations. It can be seen that the low-energy shoulder of the water absorption peak is displaced further toward lower wave numbers with increasing acid contaminations. It can furthermore be seen that the absorption in the range around 3660 cm$^{-1}$ disappears with increasing acid contamination. In the range around 3900 cm$^{-1}$, prominent absorptions do not occur in any spectrum, and therefore this range is suitable as a reference range 17 in order to show how strongly the light is allowed to pass through the hydraulic fluid 10.

Figure 15:
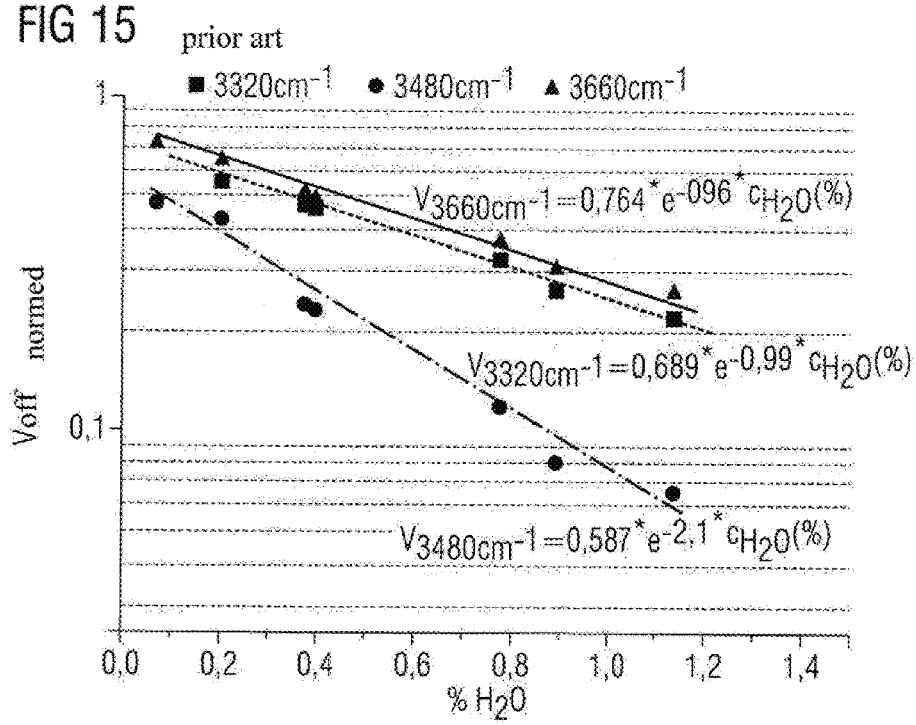
FIG. 15 shows the decrease of the light intensity in the monitoring ranges marked in FIG. 14 as a function of the water contamination.
Figure 16:
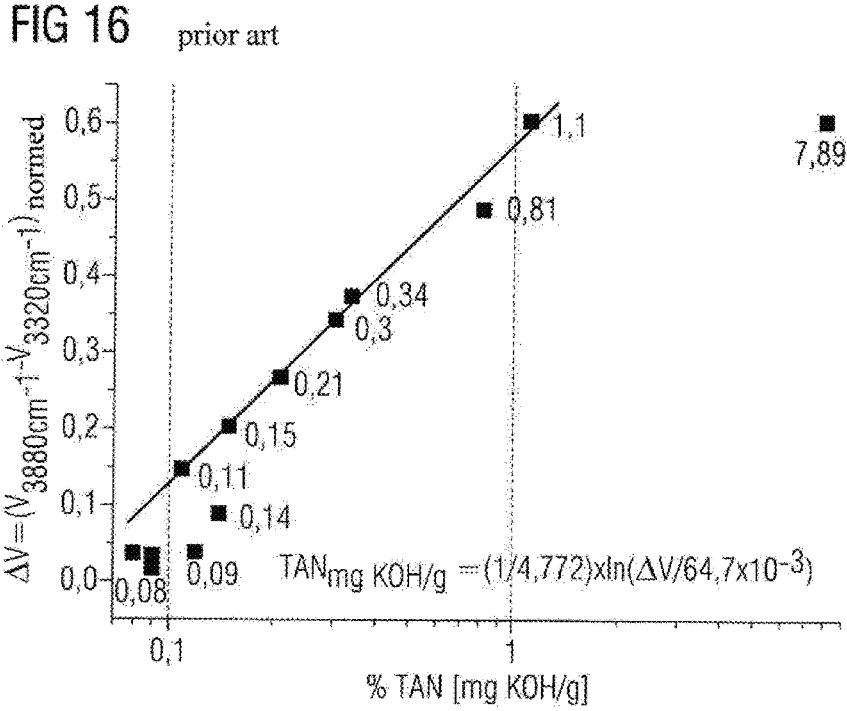
FIG. 16 shows the acid sensitivity of a contamination recording apparatus.

As can be seen in FIG. 15, the range around 3500 cm$^{-1}$ has the greatest dependency on a water contamination out of the three ranges marked, and is therefore suitable for examining the water contamination of Skydrol. The acid contamination is carried out by observing the range around 3660 cm$^{-1}$. To this end, the detected absorption may be normalized by subtracting the absorption in the range around 3320 cm$^{-1}$ and, as shown in FIG. 16, plotted against the acid number TAN.

Figure 17:
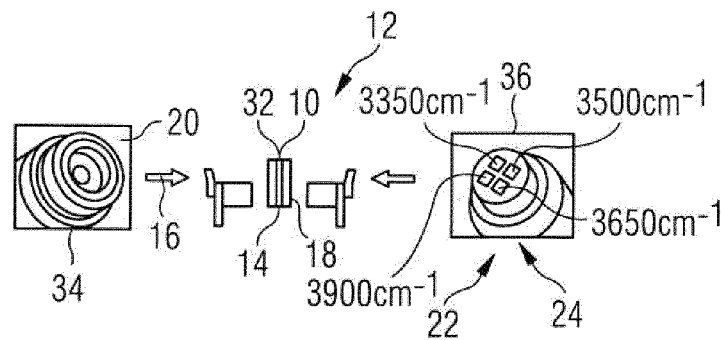
FIG. 17 shows the structure of a contamination recording apparatus using MIR light.

FIG. 17 shows a disassembled structure of the contamination recording apparatus 12 using MIR light 16. The hydraulic fluid 10 is conveyed through between two sapphire windows 18. An IR emitter 20, for example a MEMS IR emitter, exposes the hydraulic fluid 10 to MIR light 16 through the sapphire window 18. In the hydraulic fluid 10, corresponding energy ranges of the incident MIR light 16 are absorbed, such that a sensor array 22 arranged opposite the IR emitter 20 can record absorption spectra. The sensor array 22 comprises four radiation thermopiles 24, each of which is particularly optimized for recording different wavelength ranges, namely one for 3350 cm$^{-1}$, one for 3500 cm$^{-1}$, one for 3900 cm$^{-1}$ and one for 3650 cm$^{-1}$.

Figure 18:
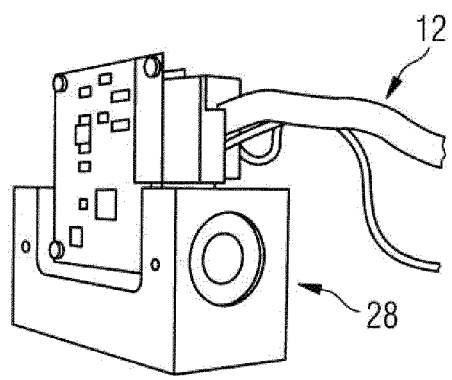
FIG. 18 shows an MIR sensor system.

FIG. 18 shows the overall structure of the contamination recording apparatus 12 using the MIR light 16.

Figure 19:
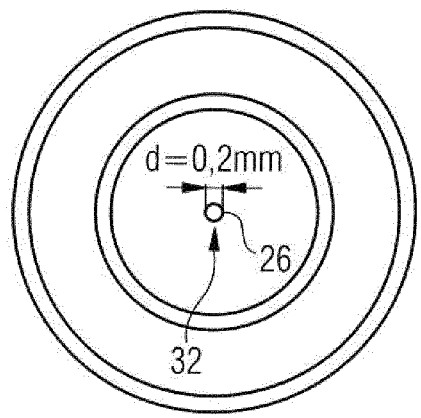
FIG. 19 shows a simplified representation of the optical light path of a conveying device, in which the hydraulic fluid flows, in the MIR sensor system of FIG. 18.

FIG. 19 shows a cross section through the conveying device 14 in which the hydraulic fluid 10 is conveyed through the contamination apparatus 12. As can be seen, a conveying channel 26 of the conveying device 14 merely has an internal diameter d of 0.2 mm, i.e. the optical light path of the light 16 emitted by the IR emitter 20 is at most 0.2 mm wide. The spectra shown in FIG. 13 and FIG. 14 were recorded with such a maximum optical light path of 0.2 mm.

In principle, although IR spectroscopy using MIR light is suitable for examining contaminations such as water and acid in hydraulic fluids 10 continuously, it has the great disadvantage that a maximum optical light path of 0.2 mm leads to the flow of the hydraulic fluid being greatly compromised upon installation in a hydraulic system 11 of an aircraft 11a, and installation in the region of the contamination recording apparatus 12 would lead to a strong pressure drop in the hydraulic fluid 10.

The contamination recording apparatus 12 shown in FIGS. 17 to 18 is therefore not very suitable for installation in hydraulic systems 11, for example of aircraft 11a.

FIG. 3 shows the structure of an embodiment according to the invention of a contamination recording apparatus having a conveying device 14 which comprises a conveying channel 26 having an internal diameter d of from 5 to 20 mm. As indicated by the arrow, the hydraulic fluid 10 in this case flows past a plurality of sensors 28, which will be explained in more detail below. The optical light path 32 between a light source and a detection device 36 is determined by the internal diameter d of the conveying channel 26.

FIG. 4 shows a sensor system 38, the optical light path 32 of which is variable.

The contamination recording apparatus 12 shown in FIG. 3 comprises a first light source 40, a second light source 42 and a third light source 44, each of which emits light in the near-infrared range (NIR light) 46. In this case, the first light source 40 emits light 46 in the wavelength range of from 2020 nm to 2150 nm, the second light source 42 emits light 46 in the wavelength range of from 1880 nm to 2000 nm, and the third light source 44 emits light 46 in the wavelength range of from 1820 nm to 1840 nm. Each light source 40, 42, 44 is respectively assigned a detection device 36, which is arranged opposite the respective light source 40, 42, 44 on the conveying device 14. In the regions in which the light sources 40, 42, 44 and the detection devices 36 are located, the conveying device 14 comprises optically transparent regions 48, which are formed by sapphire windows 18.

The light sources 40, 42, 44 are preferably formed by LEDs 50 and/or lasers 52, and the detection devices 36 comprise detectors 54 having photodiodes 56 consisting of semiconductor material, for example InGaAs or Ge.

An acid number monitoring device 58 and a particle recording device 60 are furthermore arranged on the contamination recording apparatus 12. The conveying device 14 also comprises optically transparent regions 48 in the regions in which the acid number monitoring device 58 and the particle recording device 60 are respectively arranged.

The acid number monitoring device 58 comprises a UV light source 62 and a UV detection device 64, which are fitted at an angle of 45° to one another on the conveying device 14.

The particle recording device 16 also comprises a light source 34, which emits UV, VIS or NIR light 46. The corresponding detection device 36 is likewise arranged at an angle of 45° to the light source 34 of the particle recording device 60 on the conveying device 14.

The contamination recording apparatus 12 is fastened in fluid communication on a hydraulic fluid line 66 of the hydraulic system 11, and has the same internal diameter d as the hydraulic fluid line 66. In the hydraulic fluid line 66, or in the hydraulic system 11, the hydraulic fluid 10 flows from a fluid source 67a shown in FIG. 1 to a fluid sink 67b shown in FIG. 1, for example to hydraulic actuators 67c, or vice versa.

In the region in which the contamination recording apparatus 12 is connected to the hydraulic fluid line 66, there is a coupling device 68, by which the contamination recording apparatus 12 can easily be coupled to the hydraulic system 11 or decoupled therefrom.

NIR light 46 results in significantly weaker absorptions than MIR light 16, but it will be shown below with the aid of FIGS. 5 to 12 that contaminations in the hydraulic fluid 10 can be monitored by using NIR light 46. Advantageously, this is supported by the special selection of the observed energy ranges.

The following spectra were recorded with an optical light path 32 of 10 mm.

Figure 5:
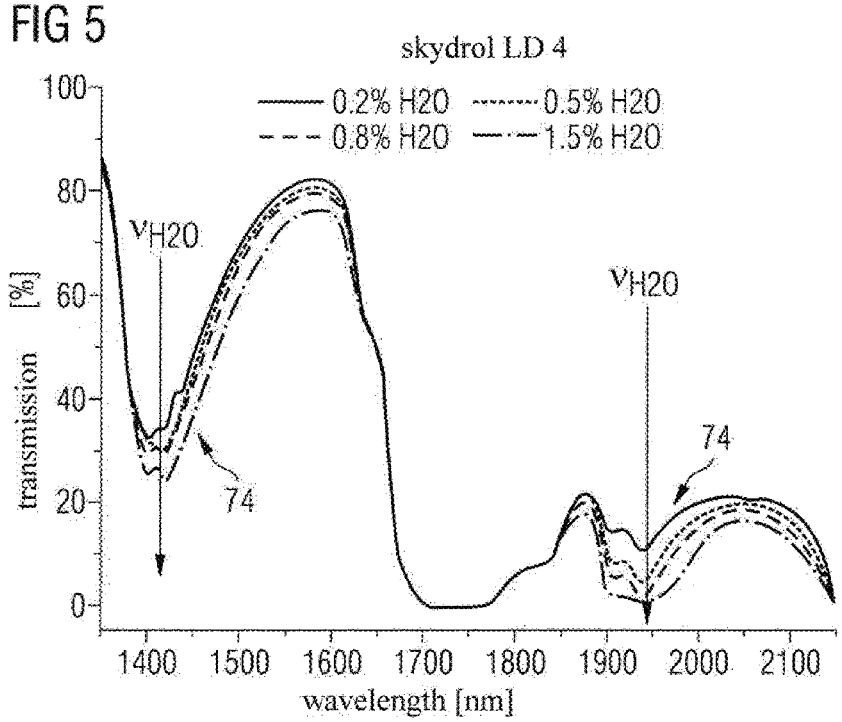
FIG. 5 shows NIR overview absorption spectra of a hydraulic fluid having different water contaminations.

FIG. 5 shows an overview spectrum in the wavelength range of between 1350 nm and 2150 nm of hydraulic fluid contaminated with different water concentrations. The spectra have two marked prominent water absorptions 74, namely at 1420 nm and at 1940 nm.

Figure 6:
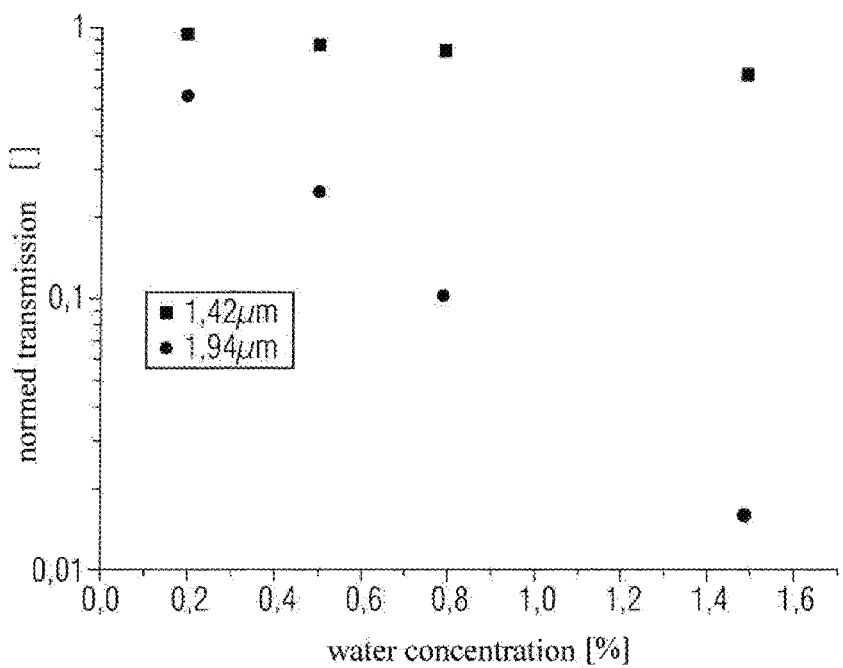
FIG. 6 shows absorption changes of the absorptions shown in FIG. 5 for different water concentration.

FIG. 6 shows the change of the absorptions with increasing water contamination in the two prominent water absorption ranges marked in FIG. 5. The change can be seen more clearly in the range around 1940 nm than in the range around 1420 nm. The range around 1940 nm therefore seems more suitable for monitoring the hydraulic fluid 10 for contaminations.

Figure 7:
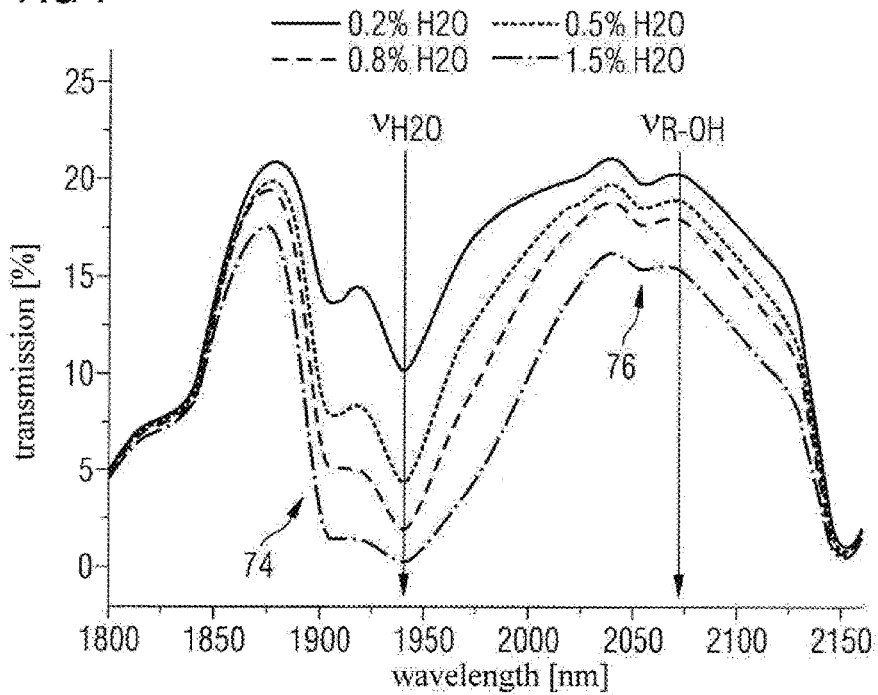
FIG. 7 shows the absorption spectrum of FIG. 5 in detail from 1800 nm to 2150 nm wavelength.

FIG. 7 shows a detail range of FIG. 5 between 1800 nm and 2150 nm. Besides the water absorption 74 around 1940 nm, the range of an alcohol absorption 76 around 2075 nm is additionally indicated. Alcohol contaminations result from hydrolysis of the hydraulic fluid 10 and are therefore an indicator of the acid contamination of the hydraulic fluid 10, which is likewise caused by hydrolysis of the hydraulic fluid 10.

Figure 8:
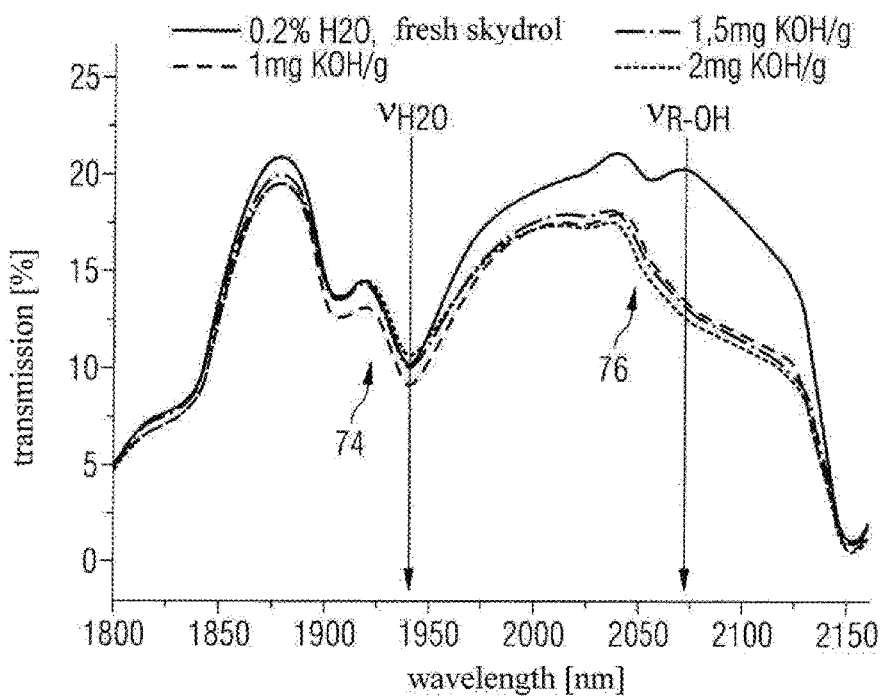
FIG. 8 shows absorption spectra for contamination of the hydraulic fluid with acid.

FIG. 8 shows the change of the range around 2075 nm with increasing acid contamination of Skydrol.

In all spectra in FIG. 5, FIG. 7 and FIG. 8, it can be seen in that no change occurs in the range around 1830 nm, either by addition of water or by the increasing acid contamination.

For monitoring of the hydraulic fluid 10, the selection ranges 78 shown in FIG. 9 are therefore selected in order to monitor the hydraulic fluid 10.

In the range between 1820 nm and 1840 nm, no absorptions occur at all, and therefore this range can be used as a reference range 17 in order to record the total light transmissivity of the hydraulic fluid 10, so that the data of the other selection ranges 78 can be normalized.

The range around 1880 nm to 2000 nm is suitable for monitoring water absorptions 74, and the range around 2020 nm to 2150 nm is suitable for recording alcohol absorptions 76, and therefore the acid number TAN.

FIG. 10 shows the arrangement of an LED 50 and a photodiode 56 with a conveying device 14, in which the hydraulic fluid 10 flows, arranged between them. In this case the optical light path 32 is variable. With such a structure, the absorption coefficient of the contamination recording apparatus 12 can be recorded. To this end, the optical light path 32 is varied and the signal of the photodiode 56 is recorded. This is represented in FIG. 11. Here, the dependency of the signal intensity on the optical light path 32 for a Ge photodiode is shown in 11a) and the dependency of the signal intensity on the optical light path 32 for an InGaS photodiode is shown in 11b). In the case of 11a), an LED 50 having an emission peak in the range of 1420 nm was used, and in the case of 11b) an LED 50 having an emission peak in the range of 1920 nm was used. In both cases, a signal intensity dependency on the optical light path 32 was determined according to the Lambert-Beer law, and so the absorption coefficient of the respective structure could be calculated (0.02 m$^{-1}$ for the Ge photodiode and 0.2059 m$^{-1}$ for the InGaS photodiode).

FIG. 12 shows the dependency of the signal intensity on the water contamination for different optical light paths 32 when using the InGaS photodiode. It can be seen that even with an optical light path 32 of 10 mm, the change of the absorption can be seen clearly, and the hydraulic fluid 10 can therefore also be monitored in this range.

The quality of hydraulic fluids 10 is extremely important in order to ensure that safety-relevant systems in aircraft 11a, for example landing flaps 80, slats and the undercarriage etc. operate correctly. Contamination of the hydraulic fluid 10 with moisture can cause serious damage to mechanical components in a hydraulic system 11. The proposed sensor 28 can be integrated into hydraulic systems 11 of aircraft 11a, in order to monitor the water content and molecular breakdown products of the hydraulic fluid 10 directly during operation.

Commercially available sensors record electrical and/or dielectric properties of the hydraulic fluid 10. Such sensors are unreliable because the electrical or dielectric properties of the hydraulic fluid 10 are not related exclusively to the relevant chemical fluid properties, for example the water content and the acid content. Optical sensors which operate in the mid-infrared range, on the other hand, have preferred sensor properties. MIR sensors, however, require a very narrow optical light path 32, and therefore block the fluid flow in hydraulic systems 11 in aircraft 11a.

A sensor 28 is therefore proposed which uses NIR light in order to record contaminations and molecular breakdown products in hydraulic fluids 10. Because NIR light 46 is absorbed significantly less in hydraulic fluids 10 than MIR light 16 is, it is possible to construct optical sensors 28 that do not block the fluid flow within hydraulic systems 11 in aircraft 11a. NIR sensors 28 can therefore be installed in already existing aircraft hydraulic systems, without interfering with the operation of the hydraulic system 11.

The sensor 28 is an optical system, which can be integrated into the hydraulic system 11 without cable feedthroughs which would need to be installed through the hydraulic fluid 10 conveyed under high pressure. Furthermore, no buffer solutions or calibration are necessary, as for example when monitoring electrical or dielectric properties. In addition, the sensor system can self-test by using light sources 34 pulsed by alternating current A/C.

In commercial aircraft 11a, landing flaps 80, slats, the tail unit and the undercarriage, i.e. all types of safety-relevant components, are driven by hydraulic actuators 67c.

Hydraulic fluids 10 in aviation must be fire-resistant, and are therefore based on phosphate esters. Such fluids are very hygroscopic, as explained, for example in the following documents:

G. E. Totten, Handbook of hydraulic fluid technology, Marcel Dekker Inc. ISBN: 0-8247-6022-0;

G. E. Totten, Handbook of Lubrication and Tribology: Application and Maintenance, CRC Press, Boca Raton, Fla., USA, 2006.

These fluids are therefore susceptible to accumulation of moisture from different sources, for example seals and compressed air reservoirs. Absorbed water in combination with elevated temperatures can furthermore lead to a reaction of the hydraulic fluid 10 with the water and thereby form acidic molecule fragments. These molecule fragments lead to corrosion of all types of metallic components in the hydraulic system 11, in particular of the actuators which drive the aforementioned safety-relevant components.

In order to avoid mechanical wear in the hydraulic system 11, the quality of the hydraulic fluid 10 must be ensured by repeated measurements of the relevant fluid properties and by suitable maintenance of the hydraulic fluid 10.

Currently, hydraulic fluid maintenance comprises the following steps:

aircraft 11a is on the ground (normally during the C check about once every three years);

tapping the hydraulic fluid system 11 of the aircraft 11a;

taking samples of the hydraulic fluid 10 from the hydraulic system 11;

dispatching the hydraulic fluid samples to chemical laboratories for analysis:

implementing corresponding fluid maintenance measures.

The analysis in chemical laboratories is time-consuming and takes about five to ten days. Normally, the aircraft 11a is already in use again when the results of the samples are provided. In the case in which the quality of the hydraulic fluid 10 lies outside predetermined limits, the aircraft 11a must then land again in order to remedy the problem. This is expensive, since the aircraft 11a is on the ground for a long time. These costs are high, in particular when maintenance work on the hydraulic fluid 10 is not planned, i.e. between the C checks.

In order to avoid unplanned maintenance work on the hydraulic fluid 10, miniaturized optical sensor systems have been developed which make it possible to monitor important quality parameters of the hydraulic fluid 10 quasi-continuously. Owing to the fact that regular measurements of the water content, the acid content of the particle content are carried out, hydraulic fluid degradation processes can be recorded and necessary maintenance work can be planned in such a way that it coincides with other maintenance work. The expensive ground time can thus be reduced.

Ideally, such monitoring systems should be simple and lightweight, and should be installable as far as possible into already existing hydraulic systems 11 of the aircraft 11a, without interfering with the routine operation of these hydraulic systems 11.

For this reason, a hydraulic fluid monitoring system has been developed which uses non-dispersive infrared (NDIR) absorption technology in order to record the water and acid content in hydraulic fluids 10 of aircraft 11a.

This monitoring system is published in the following documents:
S. Paul et al., Chemical Contamination Sensor for Phosphate Ester Hydraulic Fluids, International Journal of Aerospace Engineering, vol. 2010, 2010, Article ID 156281;
S. Paul et al., Multi-Parameter Monitoring System for Hydraulic Fluids, Technisches Messen, 78 (2011) 5/DOI 10.1524/teme.2011.0117, Oldenbourg Wissenschaftsverlag 2011;
EP 11003162.2.

The central concept in this sensor 28 is monitoring of the OH absorptions in the hydraulic fluid 10, in order to examine the amount of absorbed water and record the molecule fragments which are associated with the formation of acid groups.

This method will be explained with the aid of the MIR spectra in FIG. 13 and FIG. 14. In their normal uncontaminated state, phosphate ester hydraulic fluids ought to exhibit no OH absorptions. A wide OH absorption in the range of 3500 cm$^{-1}$, however, is present in the case of liquid water. Alcohols result in OH absorptions which are low-frequency shifted relative to the water absorption 74. This is in particular the case for butanol and phenol, i.e. the typical breakdown products of phosphate esters.

FIG. 3 shows the IR transmission spectra of pure and water-contaminated samples of Skydrol LD4, the optical light path 32 being 0.2 mm.

FIG. 4 shows the IR transmission spectra of water-contaminated and additionally heat-treated Skydrol LD4 for an optical path length 32 of 0.2 mm.

The spectra shown in FIG. 3 clearly show that the water content in Skydrol LD4 can be determined straightforwardly by changes in the optical transmission around 3500 cm$^{-1}$. Titration of these water-contaminated samples furthermore shows that such liquids are not acidic. This is because neutralization was achieved in each case by using less than 0.1 mg KOH/g of fluid.

The effect of the heat treatment on the water absorption line around 3500 cm$^{-1}$ is shown in FIG. 14. The spectra a) and b) show the state before the heat treatment. The spectra c), d) and e) show what happens when the same liquid samples are additionally heat-treated. The acid number 10 in c), d) and e) reaches values in the range of from 1 to 2 mg KOH/g. In the case of merely dissolved water, the O—H absorption is more or less symmetrical with respect to the water absorption line around 3500 cm$^{-1}$, irrespective of the water content which has been added. In the case of the heat treatment, the O—H absorption is clearly red-shifted to lower photon energies. In addition, the symmetry around 3500 cm$^{-1}$ is clearly destroyed.

The three marked regions in FIG. 14 show three measurement regions which are used in MIR monitoring systems. The fourth range shows the spectral position of a reference range 17. Extensive tests have shown that the optical transmission of the fluid is not influenced by chemical changes within the hydraulic fluid 10 in this fourth spectral window. This fourth window can therefore be used to monitor the transparency of the sapphire window 18 and to record thermal degradations of the light source 34 for MIR light 16.

FIG. 15 shows how the transparency in the three measurement ranges changes when the water content in the hydraulic fluid 10 is increased. The transparency of the range around 3500 cm$^{-1}$ decreases rapidly with an increasing water concentration. The two neighboring ranges are reduced in an approximately similar way, and significantly less than the transparency of the range around 3500 cm$^{-1}$.

The curve with the steepest slope relates to the absorption bands in the middle around 3480 cm$^{-1}$, and the flatter curves relate to the higher-energy and lower-energy absorption bands around 3660 cm$^{-1}$ and 3320 cm$^{-1}$. The signals were normalized by the reference range around 3875 cm$^{-1}$.

FIG. 16 shows the acid sensitivity of the sensor system. The difference in the signals in the range around 3660 cm$^{-1}$ and 3320 cm$^{-1}$ shows a logarithmic dependency on the acid number in the range of from 0 to mg KOH/g of fluid. As shown in FIG. 16, the transparency difference of the range around 3350 cm$^{-1}$ and the range around 3650 cm$^{-1}$ increases logarithmically with an increase in the acid number TAN. For higher TAN values, saturation of the sensor signal is observed. Quantitative evaluation of TAN values of more than 1 mg KOH/g is therefore not possible with this sensor system.

The basic structure of an MIR sensor system is shown in FIG. 17, FIG. 18 and FIG. 19.

The IR detection system comprises a MEMS-based IR emitter 20, an optical light path 32 and a quadruple radiation thermopile 24 as an IR sensor array 22. FIG. 18 shows the entire sensor system. FIG. 19 is a view into the fluid channel, which shows that the optical light path 32 is very narrow with d=0.2 mm. This internal diameter d blocks the fluid flow through the sensor 28.

Although FIGS. 13 to 16 have clearly shown that MIR is suitable for monitoring the relevant fluid parameters, in particular FIG. 19 shows the practical limitations of an MIR sensor. FIG. 19 shows the very narrow optical light path 32 which blocks the fluid flow through the sensor 28. This is due to the fact that the MIR ground state absorption bands are strongly absorbed. In a hydraulic system 11 of an aircraft 11a, however, such flow blockages are not tolerable. In order to install a monitoring system in a hydraulic system 11 of an aircraft 11a, it is therefore necessary for the sensor system to be accommodated in a bypass region which is separated from the main hydraulic system by bypass valves. This makes the monitoring system relatively large and heavy, so that in principle it can only be used when the aircraft 11a is on the ground where special measurement routines can be carried out without interfering with the flight operation. This is because as soon as the hydraulic fluid 10 is conveyed through such a narrow system, a large pressure drop results. In an aircraft 11a, such high pressure differences only occur between high- and low-pressure regions of the hydraulic system 11 in the aircraft 11a. Sensible positions of the MIR sensor system are therefore restricted to positions which are close to the hydraulic fluid reservoir 67a and/or the hydraulic pump.

Owing to these disadvantages, it has not so far been possible to install MIR monitoring systems directly in aircraft 11a. They can however be used on the ground for maintenance work, and to this end fastened on maintenance vehicles. It can, however, happen that impurities are in this case transferred via the maintenance vehicle from one aircraft 11a to another.

In order to allow online monitoring of the hydraulic fluid 10 during a flight, the fluid blockages in the measurement system must be eliminated. This means that a fluid monitoring system is advantageously fitted in a hydraulic system 11 in such a way that a short section of a hydraulic system line is removed and replaced by another line section with the same internal diameter d, the other line section containing the necessary sensor components. These requirements can be satisfied by using NIR light 46.

NIR absorption bands result from anharmonic molecular vibrations. Compared with the MIR ground state molecular absorptions, the absorptions in the NIR harmonic ranges are much less. This means that longer light absorption paths are required in order to achieve the same attenuation of the exciting light source 34. Typically, the absorption changes by one order of magnitude at the transition to the next-higher harmonic absorption.

Table 1 shows overtones and combination bands of molecular species which may be envisioned for the fluid monitoring. This table shows, for example, that the water absorption can be observed in a plurality of spectral ranges, for example at 1000 nm, 1400 nm and 1900 nm (O—H harmonics). Alcohols, which are hydrolysis products of phosphate ester fluids, can likewise be recorded in neighboring spectral ranges.

TABLE 1

| Functional Groups | | | | | | | | | | | | | | | | | | | | | | | |
|---|---|---|---|---|---|---|---|---|---|---|---|---|---|---|---|---|---|---|---|---|---|---|---|
| Water | H2O | | | | | | | | | | | | | | | | | | | | | | |
| A.AO | ROH | | | | | | | | | | | | | | | | | | | | | | |
| O.C | RCOOH | | | | | | | | | | | | | | | | | | | | | | |
| O.C | RCOOR' | | | | | | | | | | | | | | | | | | | | | | |
| A.AO | ArOH | | | | | | | | | | | | | | | | | | | | | | |
| A.AO | RNH2 | | | | | | | | | | | | | | | | | | | | | | |
| O.B | CONH2 | | | | | | | | | | | | | | | | | | | | | | |
| O.B | ArCH | | | | | | | | | | | | | | | | | | | | | | |
| O.B | RNHR' | | | | | | | | | | | | | | | | | | | | | | |
| O.B | CONHR | | | | | | | | | | | | | | | | | | | | | | |
| O.B | SH | | | | | | | | | | | | | | | | | | | | | | |
| O.B | CH | | | | | | | | | | | | | | | | | | | | | | |
| O.C | CHO | | | | | | | | | | | | | | | | | | | | | | |
| IC | CH2 | | | | | | | | | | | | | | | | | | | | | | |
| IC | CC | | | | | | | | | | | | | | | | | | | | | | |
| IC | CH3 | | | | | | | | | | | | | | | | | | | | | | |
| λ nm/10³ | | 7.5 | 8.5 | 9.5 | 10.5 | 11.5 | 12.5 | 13.5 | 14.5 | 15.5 | 16.5 | 17.5 | 18.5 | 19.5 | 20.5 | 21.5 | 22.5 | 23.5 | 24.5 | | | | |
| λ cm⁻¹/10³ | | 13.5 | 11.8 | 10.5 | 9.5 | 8.7 | 8 | 7.4 | 6.9 | 6.5 | 6.1 | 5.7 | 5.4 | 5.1 | 4.9 | 4.7 | 4.4 | 4.3 | 4.1 | | | | |

3. Overtone
2. Overtone
1. Overtone
Combination Band

NIR absorption bands of the important functional groups in lubricant fluids are shown in Table 1. I.C. means the original oil composition, O.C. oxidation component, A.AO additional antioxidant and O.B. other oil bands depending on the fluid.

FIG. 5 shows the IR transmission spectra of water-contaminated samples of Skydrol LD4 for an optical light path 32 of 10 mm. The data of FIG. 5 clearly show that the dissolved water content in Skydrol LD4 can readily be recorded by changes in the optical transmission in the range of the first harmonic and in the range of a combination band of fundamental vibrations. Clear water absorption peaks are visible at 1420 nm and 1940 nm, stronger absorptions occurring at 1940 nm. Titration of these water-contaminated samples has shown that the fluids studied are not acidic. This is because neutralization was achieved in each case by using less than 0.1 mg KOH/g of hydraulic fluid 10.

FIG. 6 shows the variation of the IR transmissions of phosphate ester hydraulic fluids, such as Skydrol LD4, with increasing water content for two prominent absorption lines, i.e. at 1420 nm and 1940 nm. The strong decrease takes place in the range of 1940 nm and the weak decrease in the range of 1420 nm.

FIG. 7 and FIG. 8 compare IR spectra of water-contaminated Skydrol LD4 samples with samples which were additionally heat-treated to form acids. Unlike in the case of MIR, the water absorption peak at 1940 nm is not low-frequency shifted when acid is formed. Rather, the spectrum for these acid-contaminated samples changes in the range of from 2040 nm to 2120 nm. This is due to the formation of alcohols, such as butanol and phenol, during the hydrolysis.

FIG. 7 shows the IR transmission of water-contaminated Skydrol LD4 and FIG. 6 shows the IR transmission of heat-treated Skydrol LD4. The acid-contaminated fluids, which contain very little water, exhibit additional spectral absorptions at 2075 nm. In all cases, the optical light path 32 was 10 nm.

FIG. 9 shows a filter selection for chemical contamination monitoring. Filters were placed at 1930 nm and 2070 nm in order to record water and acid concentrations. The filter at 1830 nm forms a reference filter.

As shown in FIG. 9, three optical windows are selected for the sensor system. The window at 1940 nm determines the water concentration, while the window at 2075 nm records the state of the acid contamination. The window at 1830 nm is used as a reference window for monitoring the transparency of the fluid and the intensity of the LED 50. This reference band is changed only little by chemical contaminations in the hydraulic fluid 10.

For practical production of a sensor system, two LEDs 50 with emission peaks at 1940 nm and 1400 nm are used as the IR emitter 20, in particular InGaAs for 1940 nm and Ge for 1400 nm as photodiodes 56 in a detector 54. The fluid measurements were carried out with the sensor system which is shown in FIG. 4. Preliminary measurements are shown in FIGS. 10 to 12. It was possible to change the absorption path length of the measurement chamber, i.e. the optical light path 32, in order to determine the absorption coefficient. As can be seen in FIGS. 11a) and 11b), the optical absorption follows the Lambert-Beer law. FIG. 12 shows how the optical absorption changes with the water concentration. Here, the change in the IR transmission of Skydrol LD4 with increasing water content in the case of measurement by the 1940 nm LED 50 for different optical light paths 32 is plotted. No optical filter was used in the region of the detector 54. It can be seen that shorter optical light paths 32 give stronger detector signals than larger optical light paths 32.

In particular, it is shown in FIG. 12 that NIR can be used in monitoring systems in order to acquire the same information as by MIR systems. At the same time, this can be carried out with optical light paths 32 which are almost two orders of magnitude larger than those in MIR systems.

MIR systems have the disadvantage that thermal light sources 34 are directional only to a small extent and have a low energy density in the relatively narrow spectral absorption lines which are of interest. In order to obtain a sufficient optical radiation density in the case of MIR systems, it is therefore necessary to operate the thermal IR emitters 20 with high temperatures. This results in high energy consumption.

NIR systems have the advantage that semiconductor elements, i.e. LEDs 50 and photodiodes 56, can be used both for the excitation region and for the detection region. Semiconductor elements have the advantage that they have a higher optical power density and a longer lifetime and are more economical, i.e. they result overall in higher sensor system reliability.

FIG. 3 shows an overview of a hydraulic fluid sensor system, in which the hydraulic fluid 10 can be examined while flowing through. All the optoelectronic sensor components are arranged around a line which has a diameter d>5 mm, in order to allow the hydraulic fluid 10 unblocked flow through an operating hydraulic system 11.

The sensor 28 comprises a conveying channel 26, which also withstands high pressures and has an internal diameter d that is large enough to allow unblocked flow of the hydraulic fluid 10 through an operating hydraulic system 11. The conveying channel 26 comprises one or more NIR sources built on, for example LEDs 50 or lasers 52, which emit NIR light 46 through the hydraulic fluid 10 via optically transparent windows that can withstand high pressure, for example sapphire windows 18. On the opposite side from each NIR source, the light 46 which is transmitted through the flowing hydraulic fluid 10 is recorded by semiconductor photodiode 56 which lie opposite the respective NIR light source 34. Each photodiodes 56 is separated from the hydraulic fluid 10 by a high-pressure resistant and optically transparent window, for example a sapphire window 18. The NIR wavelengths of the IR emitters 20 are selected in such a way that relevant fluid properties can be monitored, as shown for example in FIG. 9.

The second light source 42 forms a reference channel for determining the optical transparency of the light path through the hydraulic fluid 10. The reference wavelength should be selected to be in a spectral range where the optical transparency of the hydraulic fluid is not influenced by water contamination and/or chemical decomposition. In the present example, the first light source 40 is formed in order to record water absorptions 74 and the third light source 44 is formed in order to record the acid number TAN of the hydraulic fluid 10.

Furthermore, the contamination recording apparatus 12 in FIG. 3 comprises additional light scattering arrangements. The exposure source of the acid number monitoring device 58 is a UV LED or a UV laser, which excites phenol fragments that have been released from the phosphate esters by chemical decomposition. The UV detection device 64 is a silicon photodiode, or a photomultiplier which is equipped with a bandpass filter that is adapted to the wavelength of the fluorescent light which is emitted by the excited phenol fragments. As already shown in EP 11003162.2, the intensity of this fluorescent light and the acid number TAN of the phosphate ester hydraulic fluid are directly related to one another. The fluorescence intensity is therefore an optical indicator of the acid content of the hydraulic fluid 10. The acid number monitoring device 58 therefore supports the monitoring of the acid number TAN by the NIR sensor 28.

In addition, the contamination recording apparatus 12 comprises a particle recording device 60 which is formed by a light scattering arrangement, so as to record the flow of particles past it in the hydraulic fluid 10. The light scattering arrangement comprises a laser 52 or an LED 50, and a photodiode 56 which is arranged at an angle of from 45° to 135° relative to the light source 34 so as to avoid direct exposure of the detector 54. Wavelengths which may be used for this light scattering arrangement lie in the NIR, VIS and UV ranges.

LIST OF REFERENCES 10 hydraulic fluid
11 hydraulic system
11a aircraft
12 contamination recording apparatus
14 conveying device
16 MIR light
17 reference range
18 sapphire window
20 IR emitter
22 sensor array
24 radiation thermopile
26 conveying channel
28 sensor
32 optical light path
34 light source
36 detection device
38 sensor system
40 first light source
42 second light source
44 third light source
46 NIR light
48 optically transparent region
50 LED
52 laser
54 detector
56 photodiode
58 acid number monitoring device
60 particle recording device
62 UV light source
64 UV detection device
66 hydraulic fluid line
67a fluid source
67b fluid sink
67c hydraulic actuator
68 coupling device
74 water absorption
76 alcohol absorption
78 selection range
80 brake flap
d internal diameter

The invention claimed is:

1. A contamination recording apparatus for recording contaminations in a hydraulic fluid to be examined flowing in a hydraulic system of an aircraft, having at least one conveying device, integratable in the hydraulic system, for conveying the flowing hydraulic fluid, having at least one light source for exposing the hydraulic fluid flowing in the conveying device to light, and having at least one detection device for recording a fraction of the light absorbed by the exposed hydraulic fluid, the at least one light source being formed in order to emit light having a wavelength in a near-infrared range;

wherein at least one first light source is formed in order to expose the hydraulic fluid to light in a wavelength range of alcohol absorptions from 2020 nm to 2075 nm, and at least one second light source is formed in order to expose the hydraulic fluid to light in a wavelength range of water absorptions from 1880 nm to 2000 nm, and at least one third light source is formed in order to expose the hydraulic fluid to light in a reference wavelength range in which neither alcohol absorptions nor water absorptions occur from 1820 nm to 1840 nm, and a detection device is assigned to each light source, and wherein the apparatus is configured to use recorded absorptions in the reference wavelength range for normalizing recorded absorptions in the other wavelength ranges, and wherein each of the at least one first, second and third light source is respectively assigned to a separate detection device which is arranged opposite the respective light source on the conveying device.

2. The contamination recording apparatus as claimed in claim 1, wherein the conveying device comprises a conveying channel for conveying the hydraulic fluid having an internal diameter of >2 mm, and/or in that the conveying device is formed in order to convey the hydraulic fluid under high pressure, and/or in that the conveying device is formed in order to convey a hydraulic fluid based on phosphate esters.

3. The contamination recording apparatus as claimed in claim 1, wherein the conveying device comprises at least one region which is optically transparent for infrared radiation and which is formed by at least one high-pressure stable window, the light source and the detection device being arranged on the optically transparent region in such a way that at least a fraction of the light emitted by the light source and transmitted through the hydraulic fluid is incident on the detection device.

4. The contamination recording apparatus as claimed in claim 1, wherein the detection device comprises a detector for recording light having a wavelength in the near-infrared range, the detector comprising at least one photodiode formed of semiconductor material.

5. The contamination recording apparatus as claimed in claim 1, wherein an acid number monitoring device for monitoring an acid number of the hydraulic fluid is arranged on the conveying device, which acid number monitoring device comprises a UV light source for exposing the hydraulic fluid to ultraviolet light, and a UV detection device for recording fluorescent light emitted by molecules in the hydraulic fluid which are excited by the ultraviolet light, and/or in that a particle recording device for recording particles contained in the hydraulic fluid is provided, which comprises a light source for exposing the hydraulic fluid to ultraviolet, visible or near-infrared light, and a detection device, for recording light scattered at the particles, the detection device arranged at an angle of from 40° to 140° with respect to a radiation direction of the light.

6. A hydraulic system for conveying a hydraulic fluid from a fluid source to a fluid sink, or vice versa, having at least one hydraulic fluid line and at least one contamination recording apparatus as claimed in claim 1.

7. The hydraulic system as claimed in claim 6,
wherein the internal diameters (d) of the at least one hydraulic fluid line and of a conveying channel of the contamination recording apparatus are substantially equal, and/or in that at least one coupling device is provided for coupling and/or uncoupling the contamination recording apparatus.

8. An aircraft having a contamination recording apparatus as claimed in claim 1.

9. A method for recording contaminations in a hydraulic fluid flowing in a hydraulic system of an aircraft, comprising:
  a) providing at least one hydraulic fluid line for conveying the hydraulic fluid in the hydraulic system;
  b) coupling a contamination recording apparatus which comprises a conveying device for conveying the flowing hydraulic fluid, a light source for exposing the hydraulic fluid flowing in the conveying device to light, and a detection device for recording a fraction of the light absorbed by the exposed hydraulic fluid;
  c) exposing the flowing hydraulic fluid to light having a wavelength in a near-infrared range;
  d) recording a fraction of the light absorbed by the exposed hydraulic fluid;
  e) repeating steps a) to d) and comparing the absorbed light fractions;
  wherein the absorbed fraction of the light in a range of alcohol absorptions, in a wavelength range from 2020 nm to 2075 nm, and in a range of water absorptions, in a wavelength range from 1880 nm to 2000 nm, and in a reference range, in a wavelength range from 1820 nm to 1840 nm, is recorded;
  wherein the hydraulic fluid flowing in the conveying device is exposed by at least a first light source that emits light in the wavelength range from 2020 nm to 2075 nm, a second light source that emits light in the wavelength range from 1880 nm to 2000 nm and a third light source that emits light in the wavelength range from 1820 nm to 1840 nm; wherein each of the at least one first, second and third light source is respectively assigned to a separate detection device which is arranged opposite the respective light source on the conveying device; and
  wherein the recorded absorbed fractions in the reference range are used for normalizing the recorded absorbed fractions in the other ranges.

10. The method as claimed in claim 9,
wherein at least one hydraulic fluid line of the hydraulic system is replaced by the conveying device of the contamination recording apparatus in step b), the internal diameter (d) of which is substantially equal to the internal diameter (d) of the hydraulic fluid line.

11. The method as claimed in claim 9,
comprising recording of the acid number of the hydraulic fluid and/or recording of a particle count in the hydraulic fluid.

* * * * *